United States Patent [19]

Georgiev et al.

[11] Patent Number: 4,691,051
[45] Date of Patent: Sep. 1, 1987

[54] ADAMANTYL PHENYL β-ALANINES

[75] Inventors: Vassil S. Georgiev, Rochester; George B. Mullen, Avon, both of N.Y.

[73] Assignee: Pennwalt Corporation, Philadelphia, Pa.

[21] Appl. No.: 870,553

[22] Filed: Jun. 4, 1986

Related U.S. Application Data

[63] Continuation-in-part of Ser. No. 691,104, Jan. 4, 1985, abandoned.

[51] Int. Cl.[4] .............................................. C07C 101/08
[52] U.S. Cl. ..................................... 562/443; 562/445
[58] Field of Search ............... 562/443, 444, 445, 499, 562/442

[56] References Cited

U.S. PATENT DOCUMENTS 3,076,800  2/1963  Grof ............................. 260/239 AL
3,119,813  1/1964  Taub ............................. 260/239 AL
3,465,034  9/1969  Gagneux et al. ................... 562/499
3,595,876  7/1971  Back et al. ........................ 562/442
3,642,878  2/1972  Kampe .......................... 260/239 AL
4,202,892  5/1980  Weiner et al. ....................... 562/499

Primary Examiner—James H. Reamer

[57] ABSTRACT

Adamantyl phenyl β-alanines having the structure:

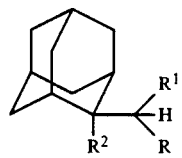

wherein R is phenyl or substituted phenyl and one of $R^1$ and $R^2$ is $NH_2$ and the other is $CO_2H$, are disclosed herein.

3 Claims, No Drawings

ADAMANTYL PHENYL β-ALANINES

RELATED APPLICATIONS

This application is a continuation-in-part of our copending application Ser. No. 691,104 filed Jan. 4, 1985 now abandoned.

FIELD OF INVENTION

This invention relates to certain adamantyl phenyl β-alanines. More particularly, it relates to 2(or 3)-(adamant-2-yl)-3(or 2)-phenyl-βalanines having the structures

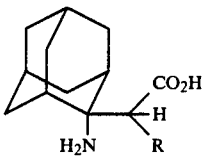

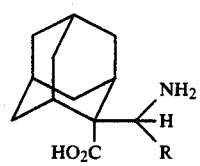

wherein R is phenyl or substituted phenyl. These compounds are prepared by the opening of an azetidinone ring wherein the azetidinone compound is subjected to alkaline conditions at elevated temperatures. More particularly, the process of preparing these compounds involves the opening of the azetidinone ring of the spiro[azetidin-2-one-4,2′(or 3,2′)-tricyclo[3.3.1.1$^{3,7}$]decane] by heating a solution of such decane in the presence of an inorganic base to preferably provide the here-to-fore difficult to obtain 3(or 2)-(adamant-2-yl)-2(or 3)-phenyl-β-alanines of the structure I or II below

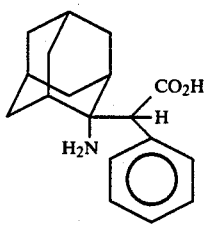

I.

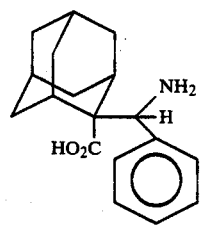

II.

STATEMENT OF THE INVENTION

This invention comprises adamantyl phenyl β-alanines having the following structures:

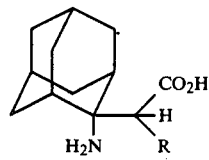

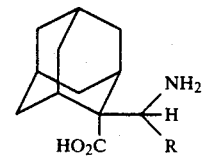

where R is phenyl or substituted phenyl.

DETAILED DESCRIPTION OF THE INVENTION

As previously set forth, the compounds of this invention have the following structures:

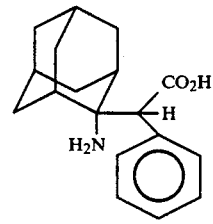

I.

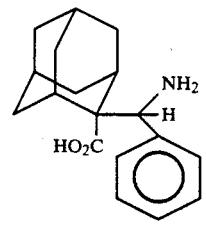

II.

The phenyl group of compounds I and II may be substituted or unsubstituted. Substituent groups include, for example, oxyalkyls (—$OC_nH_{2n+1}$) which preferably have from 1 to 8 carbon atoms, more preferably less than 4 carbon atoms.

The compounds of this invention are prepared from azetidinone ring compounds as disclosed in copending application Ser. No. 653,632 filed Sept. 24, 1984. In general, these adamantane-spirolactam derivatives may be prepared by the Grignard reaction of 2-adamantanone or its spiro-oxirane derivative with an appropriate organomagnesium halide to provide a corresponding 2-substituted-adamantan-2-ol. Dehydration of the resulting decanol compound forms the corresponding unsaturated analog which, in turn, when subjected to cycloaddition with chlorosulfonyl isocyanate, provides the N-chlorosulfonyl adamantane-spiro-azetidin-2-one. Reductive dechlorosulfonation of the spiroazetidinone furnishes the corresponding β-lactam analog.

The compounds produced in accordance with the above process descriptions are the starting compounds of this invention; their general structure is shown as follows:

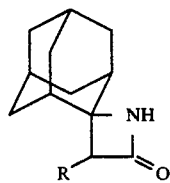

III.

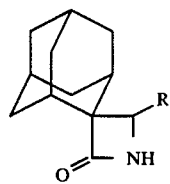

IV.

R in the above formulas III and IV is a substituent including phenyl or substituted phenyl groups.

The compounds of formulas III and IV are treated with an alkaline reagent to provide β-amino acids. For the ring-opening reaction to proceed at a reasonable pace, the azetidinone compound is dissolved in an organic solvent inert to the dissolved compound. Examples of these solvents include lower alkanols ($C_1$-$C_6$ alkyl alcohols), e.g., ethanol, isopropanol, butanol and the like. The preferred solvent is an alkanol having less than four carbons, preferably ethanol. The concentration of the azetidinone in the solvent can range from an amount up to its solubility in the solvent to as low as about 2% based on the weight of the solution. It is preferred that the azetidinone be present at a concentration of about 10% based on the weight of the solution.

The alkaline medium used for treatment of the azetidinone is an aqueous solution of any inorganic base including, for example, oxides and hydroxides of alkali metals and alkaline earth metals, ammonium hydroxide and the like. Preferably, the alkaline medium is an aqueous solution of an alkali metal hydroxide including potassium, sodium, lithium, cesium and rubidium hydroxide, most preferably potassium. The alkaline compound (or compounds) in the aqueous solution is preferably used at a concentration of between 5 and 15% based on the weight of the solution of the amount of basic solution used will preferably provide at least 25% of alkaline compound, based on the weight of the azetidinone compound in solution, to the ring-opening reaction.

The temperature at which the ring-opening process is carried out ranges from about 50° C. up to reflux temperature at ambient pressure. Reflux temperature is preferably used.

The time during which the process is carried out ranges from about 8 hours up to about 48 hours, preferably about 12 to 20 hours under reflux condition.

Subsequent to treatment with the inorganic base to produce a ring-opening, the product may be precipitated from solution with a mineral acid and recrystallized from water.

Pharmaceutically acceptable salts of the compounds of this invention and various inorganic and organic acids and bases are included within the scope of the disclosure. Suitable pharmaceutically acceptable bases are any non-toxic inorganic or organic cations which form salts within the acids of structures I and II. Illustrative inorganic cations which form suitable salts include, sodium, potassium, magnesium, calcium, aluminum and zinc. Illustrative organic amines which form suitable cations are ethanolamine, diethanolamine, tromethamine and meglumine.

Suitable pharmaceutically acceptable acid addition salts are any nontoxic inorganic or organic acid addition salts of the compounds of this invention. Illustrative inorganic acids which form suitable salts include hydrochloric, hydrobromic, sulfuric and phosphoric acids. Illustrative of organic acids which form suitable salts are acetic, lactic, succinic, fumaric, malic, maleic, tartaric, citric, benzoic, methanesulfonic and carbonic acids. Quaternary salts of the compounds of formulas I and II with methylhalides are also suitable.

The following examples are set forth to demonstrate the preparation of compounds included in this invention and the method for preparing such compounds.

EXAMPLE 1

2-[Amino(p-methoxyphenyl)methyl]tricyclo[3.3.1.1$^{3,7}$]decane-2-carboxylic acid was prepared from 4-(p-methoxyphenyl)-spiro[azetidin-2-one-3,2'-tricyclo[3.3.1.1$^{3,7}$]decane] in accordance with the procedure of Example 2 below. The product had a melting point of 205°–213° C. (water) (dec.).

Anal. Calcd. for $C_{19}H_{26}ClNO_3$ (as the HCl salt): C, 64.86; H, 7.45; Cl, 10.08; N, 3.98. Found: C, 63.48; H, 7.93; Cl, 9.75; N, 3.59.

EXAMPLE 2

α-[2-Amino-tricyclo[3.3.1.1$^{3,7}$]dec-2-yl]benzeneacetic acid was prepared from 3-phenyl-spiro[azetidin-2-one-4,2'-tricyclo[3.3.1.1$^{3,7}$]decane] by treating a solution of 3.22 g (0.012 mol) of the latter compound dissolved in 30 ml. of ethanol with 30 ml. of a 10 weight % aqueous solution of potassium hydroxide and refluxing the reaction mixture for 18 hours. After cooling to ambient temperature, the product was precipitated with concentrated hydrochloric acid and recrystallized from water. 2.85 g (83 wt. %) of the α-[2-amino-tricyclo[3.3.1.1$^{3,7}$]dec-2-yl]benzeneacetic acid was obtained. Mp. 169°–172° C. (dec.).

Anal. Calcd. for $C_{18}H_{23}NO_2 \cdot H_2O$: C, 71.25; H, 8.31; N, 4.62. Found: C, 71.80; H, 8.23; N, 4.41.

The compound of the above Example 2 was tested in vitro in a broth dilution test (homogenized) as described, for example, in "Antibiotics in Laboratory Medicine", Ed. Victor Lorian, M. D., Williams and Wilkins, 1980. The compound was found to be active against *S. aureus* (333–666 MIC), *S. pyogenes* (333–666 MIC), *K. pneumoniae* (>1000 MIC) and *P. vulgaris* (>1000 MIC).

Appropriate calibration with known agents permits the quantitative calculation of the minimal inhibitory concentration (MIC, expressed in micrograms per milliliter) causing complete inhibition of growth for the test compound. The compounds of this invention may be useful for the treatment or prevention of bacterial infection in warm-blooded animals and for the treatment of materials subject to bacterial contamination or deterioration.

For pharmaceutical purposes, the compounds of this invention can be administered to warm-blooded animals perorally or parenterally as active ingredients in customary dosage unit compositions. These compositions consist essentially of a dosage unit form containing the active ingredient and at least one inert pharmaceutical carrier. Dosage unit forms contemplated by the present invention include tablets, capsules, solutions, suspensions, lozenges, coated pills and parenteral compositions such as intramuscular, intravenous or intradermal preparations. Sustained release dosage forms are also contemplated where the active ingredient is bound to an ion exchange resin which, optionally, can be coated with a diffusion barrier coating to modify the release properties of the resin.

The quantity of active ingredient administered in such dosage forms can vary over a wide range depending upon the mode of administration, the size and weight of the patient and whether the nature of the treatment is prophylactic or therapeutic in nature. In general, dosage unit forms contain from about 500 mg to 3 g of the active ingredient, and in man, the dose is administered from 1 to 4 times daily. The total daily dosage will be from about 500 mg to 12 g, although lower and higher amounts can be use. A preferred total daily dose would be from 2 g to 10 g of active ingredient.

Pharmaceutical carriers or excipients used in the preparation of pharmaceutical compositions may be either organic or inorganic, solid or liquid in nature. Suitable solid excipients include gelatin, microcrystalline cellulose, lactose, starches and magnesium stearate. Suitable liquid excipients include water and alcohols such as ethanol, benzyl alcohol and polyethylene glycols. In general, the preferred liquid excipients particularly useful for injectable preparations include water, saline solution, dextrose solution and glycol solutions such as aqueous propylene glycol or aqueous polyethylene glycol. The properties of the formulations may be enhanced by the addition of one or more adjuvants possessing properties as viscosity enhancers, surfactants, pH modifiers, preservatives, sweeteners, stability enhancers, coloring agents, suspending agents, granulating agents, coating agents, disintegration modifiers, propellants, emulsifying agents and humectants.

We claim:

1. Adamantyl phenyl β-alanines having the structure:

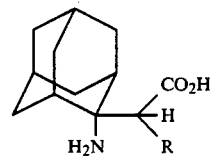

where R is phenyl or phenyl substituted with oxyalkyls having from 1 to 8 cabon atoms.

2. The adamantyl phenyl β-alanine of claim 1 wherein the substituent group has less than 4 carbon atoms.

3. The adamantyl phenyl β-alanine of claim 1 wherein the R is phenyl.

* * * * *